United States Patent
Sloan

(10) Patent No.: US 10,492,982 B2
(45) Date of Patent: *Dec. 3, 2019

(54) LINEAR MOTION MALE SEXUAL STIMULATION DEVICE

(71) Applicant: Brian Sloan, Skokie, IL (US)

(72) Inventor: Brian Sloan, Skokie, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/373,529

(22) Filed: Apr. 2, 2019

(65) Prior Publication Data

US 2019/0307636 A1    Oct. 10, 2019

Related U.S. Application Data

(63) Continuation of application No. 16/045,705, filed on Jul. 25, 2018, now Pat. No. 10,272,011.

(60) Provisional application No. 62/655,712, filed on Apr. 10, 2018.

(51) Int. Cl.
*A61F 5/00* (2006.01)
*A61H 19/00* (2006.01)
*A61H 23/02* (2006.01)

(52) U.S. Cl.
CPC ......... *A61H 19/32* (2013.01); *A61H 23/0254* (2013.01); *A61H 2201/5023* (2013.01)

(58) Field of Classification Search
CPC ......... A61H 19/00; A61H 19/30; A61H 19/32
USPC ...................................... 600/38–41
See application file for complete search history.

(56) References Cited

U.S. PATENT DOCUMENTS

| | | | |
|---|---|---|---|
| 10,272,011 B1 * | 4/2019 | Sloan | A61H 1/00 |
| 2013/0281776 A1 | 10/2013 | Levy | |
| 2013/0289345 A1 | 10/2013 | Dorronsoro Rueda | |
| 2016/0279020 A1 | 9/2016 | Timmermans | |
| 2018/0140502 A1 | 5/2018 | Shahoian et al. | |

\* cited by examiner

*Primary Examiner* — John P Lacyk
(74) *Attorney, Agent, or Firm* — Brian R. Galvin; Brian S. Boon; Galvin patent Law LLC

(57) ABSTRACT

An electromechanical device for male sexual stimulation that uses a reciprocal linear motion similar to sexual intercourse, and wherein the penis remains fully inserted during use. The reciprocal linear motion is generated by a small motor which drives a screw and nut mechanism, to which a bracket and gripper is attached. Inserted into the gripper is a flexible sleeve. A penis may be inserted into the device inside the flexible sleeve. The movement of the gripper and sleeve against the penis provides pressure and motion against the penis inside the sleeve in a manner similar to sexual intercourse. The speed, pattern, and location of the motion can be controlled by the user through controls on the outside of the device.

5 Claims, 7 Drawing Sheets

LINEAR MOTION MALE SEXUAL STIMULATION DEVICE

CROSS-REFERENCE TO RELATED APPLICATIONS

This application is a continuation of U.S. patent application Ser. No. 16/045,705 titled "LINEAR MOTION MALE SEXUAL STIMULATION DEVICE", filed on Jul. 25, 2018, which claims priority to U.S. provisional patent application Ser. No. 62/655,712, titled "LINEAR MOTION MALE SEXUGRIPPERION DEVICE" and filed on Apr. 10, 2018, the entire specification of which is incorporated herewith by reference.

BACKGROUND

Field of the Art

The present invention is in the field of devices for sexual stimulation, and more particularly in the field of devices for male masturbation.

Discussion of the State of the Art

The following is a tabulation of some prior art that presently appears relevant:

| U.S. patent applications | | | |
|---|---|---|---|
| Document Number | Kind Code | Publication Date | Applicant |
| 20160279020 | A1 | 29 Sep. 2016 | KIIROO B.V. |

| Foreign Patent Documents | | | | |
|---|---|---|---|---|
| Document Number | Kind Code | Publication Date | Country Code | Applicant |
| 2777679 | A1 | 17 Sep. 2014 | EP | E-Process Consulting and Management 2013, .S.L. |

There are various male sexual stimulation devices known in the prior art. The mechanisms by which stimulation is provided in these devices generally fall into one of five basic types: manual sheath mechanisms, vibratory mechanisms, suction mechanisms, constriction mechanisms, and direct electrical stimulation mechanisms. All of the existing mechanisms have one or more significant disadvantages, including non-ideal stimulation, possible release of bodily fluids, difficulty of use, and inability to customize the speed, pattern, and location of stimulation.

What is needed is a male masturbation device that provides a better user experience by providing optimal stimulation while eliminating the disadvantages of existing devices.

SUMMARY

Accordingly, the inventor has conceived and reduced to practice, according to a preferred embodiment, a linear motion male sexual stimulation device that provides a better user experience by providing an optimal linear stroking motion with optimal pressure, automation of the stroking motion, and user control over the speed, pattern, and location of the stroking motion, all while containing the penis and any bodily fluids fully inside the device.

In a preferred embodiment, the device is a small handheld unit powered by a low voltage, external direct current (DC) power source. Inside the device is a framework to which the mechanical parts of the device are attached. Attached to the framework is a small DC motor, which drives the stimulation mechanism. A screw shaft is affixed to the shaft of the DC motor, such that the screw shaft rotates as the shaft of the DC motor rotates. The polarity of voltage to the DC motor may be reversed so that the motor shaft rotates both clockwise and counter-clockwise. An optional gear mechanism between the motor shaft and screw shaft adjusts the ratio of motor shaft turns to screw shaft turns. A nut is placed around the screw shaft and attached to a bracket, which is held in a particular orientation by guide rods, such that the nut and bracket travel in a linear motion as the screw shaft is turned. Affixed to the bracket is a gripper, which travels in a linear motion along with the bracket. A flexible sleeve made of thermoplastic elastomer (TPE) or thermoplastic rubber (TPR) or silicone is inserted through hole in the framework and through the gripper. The end of the sleeve is held in place on the opposite end of the gripper by a ridge near the end of the sleeve. The housing of the device is made of plastic, and is attached to the framework in such a way as to provide additional support and structure to the device. User controls in the form of buttons or dials are built into the housing, and a grippable surface may be molded to the outside of the housing. The housing has an opening at one end, into which the flexible sleeve is inserted. The penis is inserted into the sleeve at the top of the device, and is stimulated by the reciprocal linear motion of the gripper and sleeve inside the device. The interior of the sleeve may or may not be textured. The user controls the speed, pattern, and location of stimulation using the controls on the outside of the housing. Magnetic sensors may be used to set limits of operation of the nut, or to ensure that the nut is at one end of its range of motion before starting operation of the device. An integrated circuit may be used to control the operation of the device. An optical rotary encoder may be used to determine the rotational speed and number of rotations of the screw shaft to control patterns of stimulation.

According to an aspect of the invention, a male sexual stimulation device is disclosed, comprising a reciprocal linear motion mechanism; a gripper attached to the reciprocal linear motion mechanism; and a flexible sleeve which is inserted into the gripper and into which the penis is inserted and remains inserted during stimulation. When the device is activated, the gripper either slides in a reciprocating linear motion along the outside of the flexible sleeve or moves the sleeve in a reciprocating linear motion along the penis, providing sexual stimulation through pressure against the penis contained in the sleeve combined with the reciprocal linear motion of the gripper.

In an aspect of an embodiment, the device may contain a heating apparatus that warms the flexible sleeve to an optimal temperature.

In an aspect of an embodiment, the device may contain a suction mechanism that provides stimulation in addition to the linear motion stimulation.

In an aspect of an embodiment, the device may contain a vibration mechanism that provides stimulation in addition to the linear motion stimulation.

In an aspect of an embodiment, the device may contain a direct electrical stimulation mechanism that provides stimulation in addition to the linear motion stimulation.

BRIEF DESCRIPTION OF THE DRAWING FIGURES

The accompanying drawings illustrate several aspects and, together with the description, serve to explain the principles of the invention according to the aspects. It will be appreciated by one skilled in the art that the particular arrangements illustrated in the drawings are merely exemplary, and are not to be considered as limiting of the scope of the invention or the claims herein in any way.

DETAILED DESCRIPTION

Figure 1:
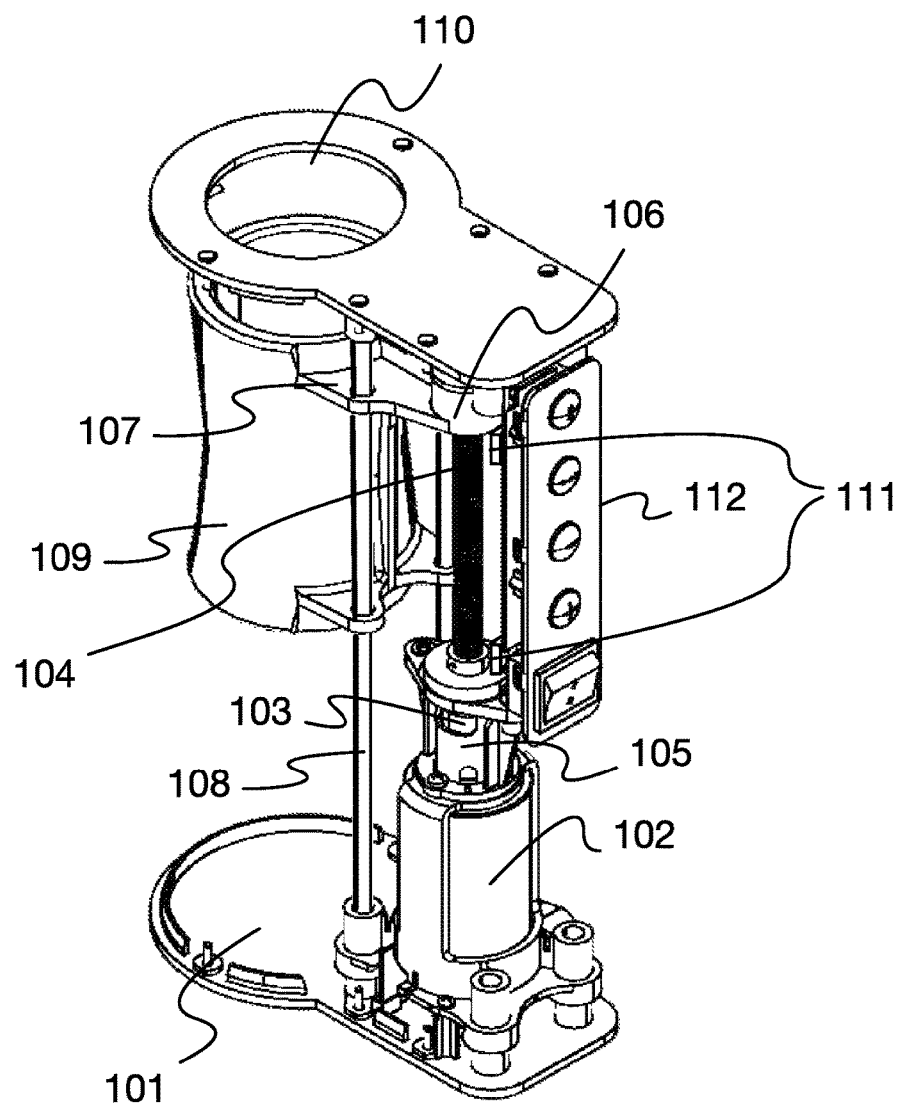
FIG. 1 shows the internal workings of an exemplary male sexual stimulation device according to a preferred embodiment.

The inventor has conceived, and reduced to practice, a linear motion male sexual stimulation device that provides a better user experience by providing an optimal linear stroking motion with optimal pressure, automation of the stroking motion, and user control over the speed, pattern, and location of the stroking motion, all while containing bodily fluids fully inside the device.

The mechanisms by which stimulation is provided in male sexual stimulation devices generally fall into one of five basic types: flexible sheath mechanisms, vibratory mechanisms, suction mechanisms, constriction mechanisms, and direct electrical stimulation mechanisms. Each of these devices has at least one significant disadvantage that is overcome by the present invention.

The sheath type device is tube-shaped device made of thermoplastic elastomer, thermoplastic rubber, silicone or other soft, flexible material, with or without an enclosing shell, into which the penis is inserted. The entire sheath device is moved up and down the shaft of the penis, causing stimulation by the friction and pressure of the sheath against the penis. Sheath type devices are used manually, requiring significant user effort, and possibly repetitive strain injury. They use a condom-like sleeve which can slip while in use, and either stretch, compress, or even slip off entirely and become lodged in the sheath. Sheath type devices expose the majority of the penis as the device is moved up and down the shaft of the penis, increasing the likelihood of release of bodily fluids outside of the device. Release of fluids outside of the device creates health and safety dangers to the user and others, can contaminate or damage other surfaces and materials onto which the fluids leak, and can make cleaning of the device itself difficult.

Vibratory mechanisms cause stimulation through oscillatory vibrations, usually created by an electric motor with an offset weight on the motor shaft. In many examples of vibratory mechanisms, for example the Hitachi Wand vibrator, the mechanism is simply pressed against the penis, causing stimulation by transmitting the vibration to the penis. In some forms of the vibratory mechanism, the penis may be inserted into the vibratory mechanism. Vibratory type devices provide a non-ideal type of stimulation, substituting vibration for the reciprocal linear motion of sexual intercourse. Further, most vibratory devices do not enclose the penis, and thus do not possess any method for containing bodily fluids. Vibratory mechanisms, in particular, also tend to produce substantial noise. While they sometimes allow the user to select different vibration patterns, such patterns do not provide much variance in stimulation, as they simply turn the device on and off at specified intervals.

Suction type devices are typically hard plastic tubes into which the penis is inserted at one end, and a suction pump is affixed to the other end. Suction type devices provide no direct stimulation through pressure or friction against the penis, and therefore provide substantially less than ideal stimulation. Suction devices may be combined with a sheath type mechanism.

A constriction type device is one in which the penis is inserted, and a set of rings either restrict blood flow back to the body, enhancing erection, or otherwise put inward radial pressure on the penis. Constriction type devices provide a non-ideal type of stimulation, substituting a squeezing motion for the reciprocal linear motion of sexual intercourse. Further, many constriction type devices do not enclose the penis, and thus do not possess any method for containing bodily fluids.

A direct electrical stimulation device is one in which the penis is stimulated through moderate voltage, very low current electrical shock. The electric shock stimulates nerve endings in the penis and may cause muscle contractions in surrounding tissue. The stimulation may be pulsed to provide different stimulation patterns. Direct electrical stimulation type devices provide a non-ideal type of stimulation, substituting electric shock pulses for the reciprocal linear motion of sexual intercourse. Further, most direction electrical stimulation type devices do not enclose the penis, and thus do not possess any method for containing bodily fluids.

The present invention overcomes the deficiencies in other mechanisms by providing ideal stimulation, similar in pressure and motion to that obtained during sexual intercourse or oral sex, in a device where the user can control the speed, pattern, and location of the motion, and where the penis remains fully enclosed in a hygienic sheath during stimulation. This device is substantially quieter than many of the alternatives, and provides substantially different stimulation in each of its user-selectable modes or patterns by allowing the user to choose where the stimulation should occur, how often it should occur at selected locations, and how fast it should occur at those locations.

The device may be controlled by an integrated circuit (IC) built into the device which controls the operation of the motor and monitors any sensors in the device. The IC may be pre-programmed or may, through a universal serial bus (USB) or other interface, be user programmable using a computer application. In either case, the IC may control the operation of the device by adjusting motor speed and direction to implement the patterns of stimulation programmed into the IC. Sensors in the device may be used to set limits of motion of the nut and screw mechanism, to ensure that the mechanism is at one end of its range of motion prior to operation, or to detect and protect against other device parameters such as motor over-heating. Sensors may be of any type suitable for the purpose, including but not limited to electrical contacts, magnetic sensors, magnetic reed switches, mechanical switches, rotational sensors, optical sensors, and temperature sensors.

In a preferred embodiment, the rotary motion from a small electric motor is translated to a linear motion through the use of a screw shaft and nut. The linear motion is translated into penile stimulation by a gripper that provides pressure against the penis through the sleeve as it glides up and down the shaft of the penis. Bodily fluids are contained within a flexible sheath inserted into the gripper, and into which the penis is inserted during use. This differs from sheath type devices in that the penis remains fully inserted in the device while in use, and the device itself is not drawn up and down the penis as with sheath type devices.

Figure 2:
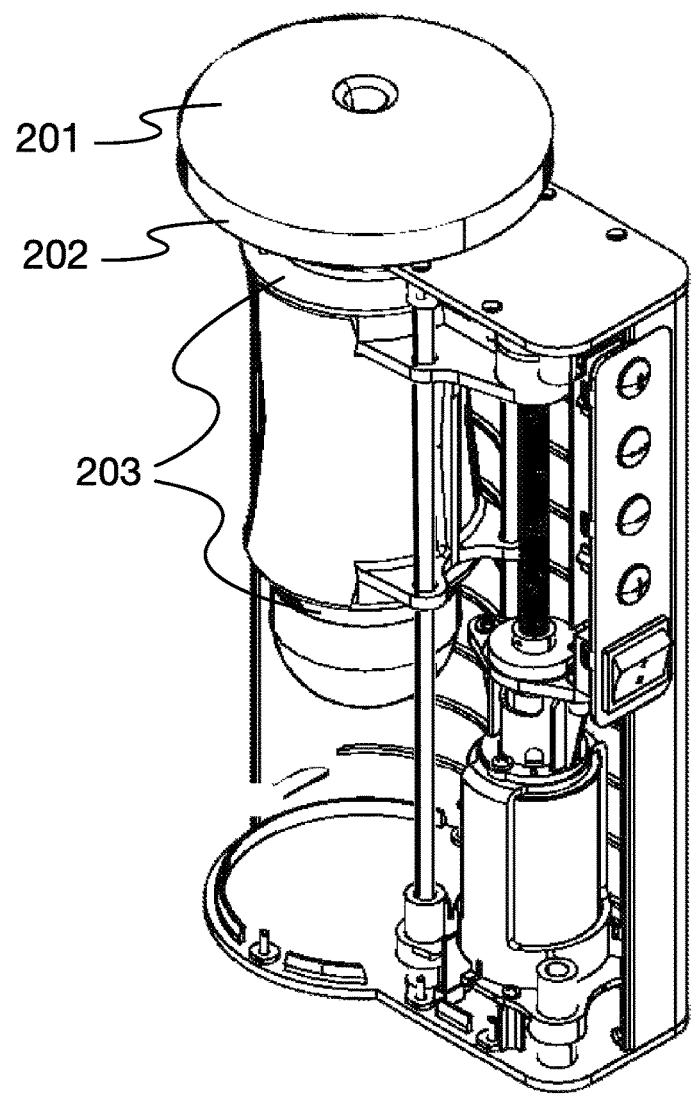
FIG. 2 shows additional components of the internal workings of an exemplary male sexual stimulation device as set forth in a preferred embodiment.

FIG. 1 shows the internal workings of an exemplary male sexual stimulation device 100 according to a preferred embodiment. In this embodiment, the device is a small handheld unit powered by a low voltage, external direct current (DC) power source. Inside the device is a framework 101 to which the mechanical parts of the device are attached. Attached to the framework 101 is a small DC motor 102 with a motor shaft 103, which drives the stimulation mechanism. A screw shaft 104 is affixed to the motor shaft 103 of the DC motor 102, such that the screw shaft 104 rotates as the motor shaft 103 of the DC motor 102 rotates. The polarity of voltage to the DC motor 102 may be reversed so that the motor shaft 103 of the DC motor 102 rotates both clockwise and counter-clockwise. A flex coupling 105 between the motor shaft 103 of the DC motor 102 and screw shaft 104 compensates for any misalignment between the two during operation. A nut 106 is placed around the screw shaft 104 and attached to a bracket 107, which is held in a particular orientation by guide rods 108, such that the nut 106 and bracket 107 travel in a linear motion as the screw shaft 104 is turned. Affixed to the bracket 107 is a gripper 109, which travels in a linear motion along with the bracket 107. A hole 110 in the framework 101, allows for the insertion of a flexible sleeve as shown in FIG. 2. Magnetic sensors 111 may be used to set limits of operation of the nut 106, or to ensure that the nut 106 is at one end of its range of motion before starting operation of the device. An integrated circuit (not visible in drawing) 112 may be used to control the operation of the device.

FIG. 2 shows additional components of the internal workings of an exemplary male sexual stimulation device 200 as set forth in a preferred embodiment. A flexible sleeve 201 made of either thermoplastic elastomer (TPE) or thermoplastic rubber (TPR) or silicone is inserted through a hole 109 in the framework 101 and through gripper 108. Sleeve 201 is prevented from accidentally slipping into device 200 by a ridge 202 at the open end of sleeve 201, and is held in the proper position by ridges 203 on the sleeve 201 at both ends of gripper 108. During operation, gripper 108 slides in a reciprocal linear motion 201 providing pressure and motion against the penis inside the sleeve 201 in a manner similar to sexual intercourse or manual masturbation. Depending on the configuration, gripper 108 may either grip sleeve 201 and move sleeve 201 along the penis, or it may slide along the outside of sleeve 201, not moving the sleeve relative to the penis. Also depending on configuration, gripper 108 may be made of rigid, semi-rigid, or compliant materials, and other shapes might be used (e.g., partial tube, ring, half-ring, multiple rings, loops of wire) and may contain rollers or bearings to increase stimulation and reduce friction against the flexible sleeve 201.

Figure 3:
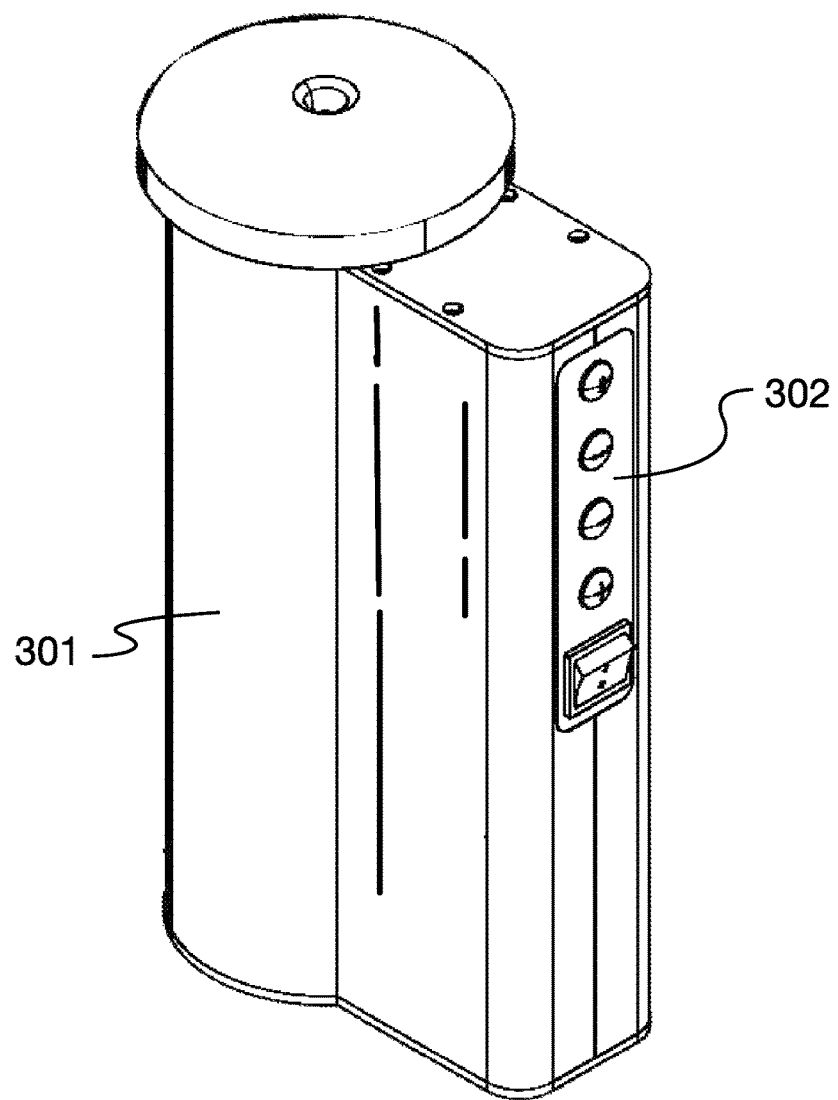
FIG. 3 shows the external structure of an exemplary male sexual stimulation device as set forth in a preferred embodiment.

FIG. 3 shows the external structure 300 of an exemplary male sexual stimulation device as set forth in a preferred embodiment. The housing 301 of the device is made of plastic, and is attached to the framework in such a way as to provide additional support and structure to the device. User controls 302 in the form of buttons and switches and their associated electronics are built into the housing. The housing has an opening at one end corresponding to the opening 109 in the framework 101, into which the flexible sleeve 201 is inserted. The penis is inserted into the sleeve 201 at the end of the device, and is stimulated by the reciprocal linear motion of the gripper 108 inside the device. The user controls the speed, pattern, and location of stimulation using the controls 302 on the outside of the housing 301.

Figure 4:
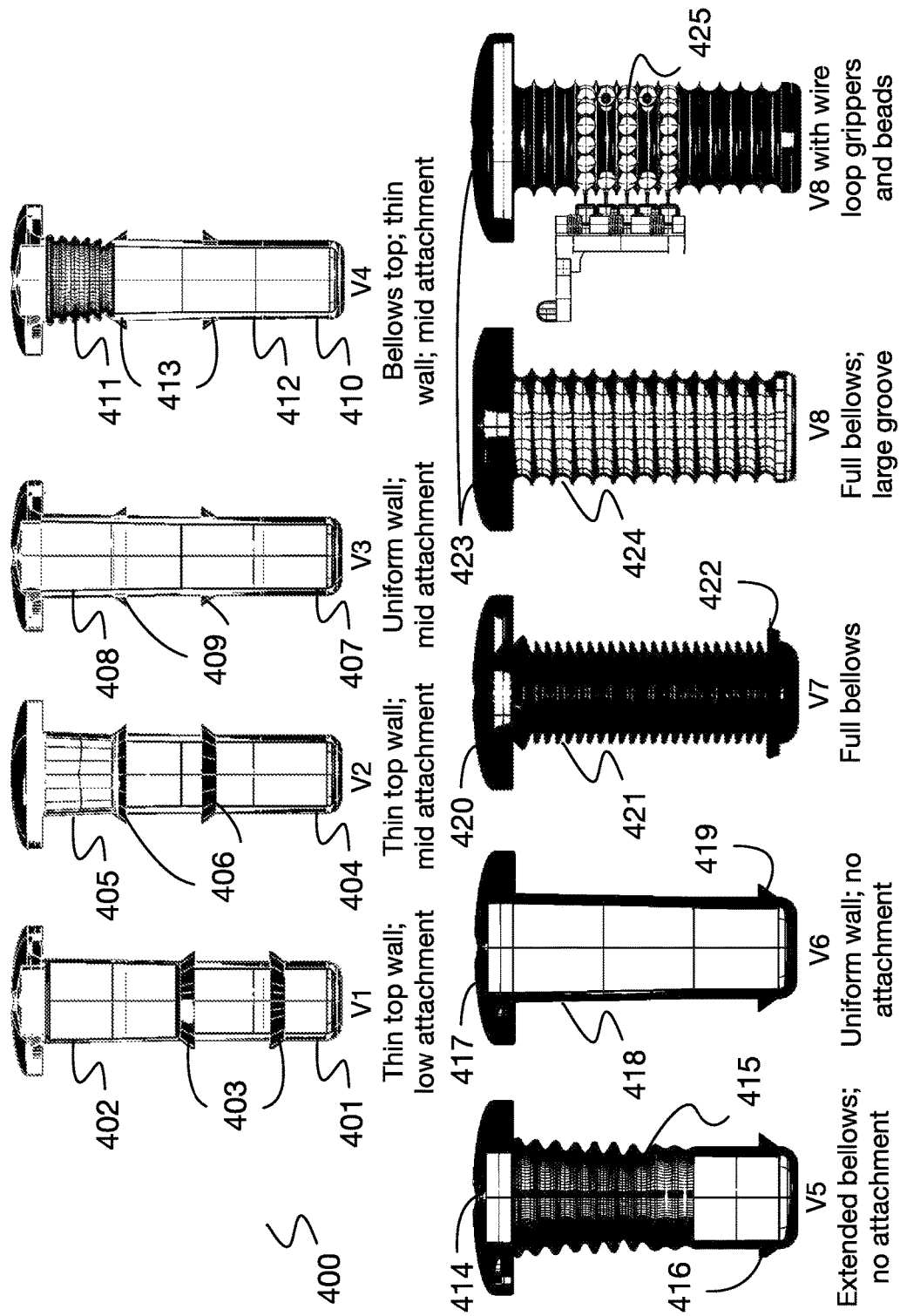
FIG. 4 shows exemplary variations of the sleeve and gripper aspects of an exemplary male sexual stimulation device as set forth in a preferred embodiment.

FIG. 4 shows exemplary variations 400 of the sleeve 201 and gripper 108 aspects of an exemplary male sexual stimulation device as set forth in a preferred embodiment. As noted above, different configurations of the sleeve 201 and gripper 108 are possible to allow optimal fit and sensation for penises of different lengths and girths, and to allow the user a choice of pressure, gripper location, and sensation. Sleeve variant one 401 has a thin top wall 402 with a low point of attachment 403 to the gripper 108. Sleeve variant two 404 has a thin top wall 405 with a middle point of attachment 406 to the gripper 108. Sleeve variant three 407 has a uniform wall thickness 408 with a middle point of attachment 409 to the gripper 108. Sleeve variant four 410 has a bellows top 411, a thin wall 412, and a middle point of attachment 413. Sleeve variant five 414 has an extended bellows 415 and no attachment to the gripper 108 other than a stopper at the end 416, allowing the gripper 108 to slide along the outside of the sleeve 414. Sleeve variant six 417 has a uniform wall thickness 418 and no attachment to the gripper 108 other than a stopper at the end 419, allowing the gripper 108 to slide along the outside of the sleeve 417. Sleeve variant seven 420 has a full bellows design 421 and no attachment to the gripper 108 other than a stopper at the end 422, allowing the gripper 108 to slide along the outside of the sleeve 420. Sleeve variant eight 423 has a full bellows design with large grooves 424 into which fits a gripper made of wire loops with beads attached 425.

Figure 5:
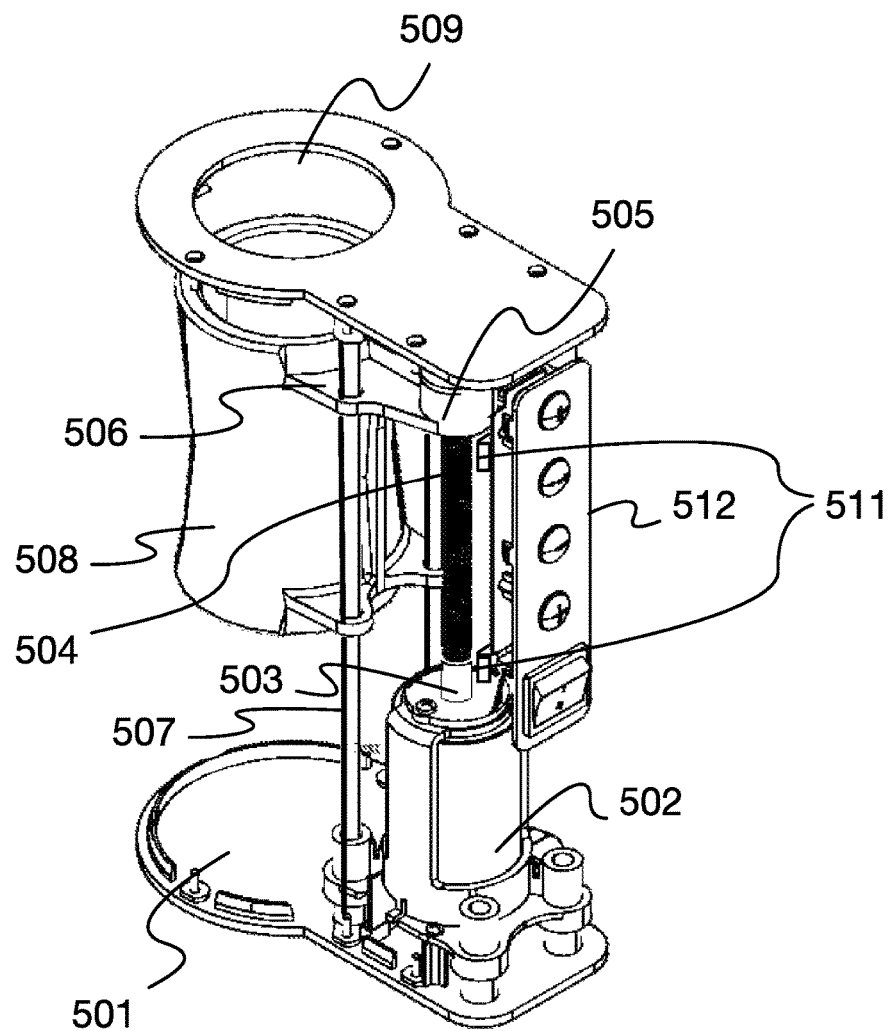
FIG. 5 shows the internal workings of an exemplary male sexual stimulation device according to another preferred embodiment.

FIG. 5 shows the internal workings of an exemplary male sexual stimulation device 500 according to another preferred embodiment. In this embodiment, the device is a small handheld unit powered by a low voltage, external direct current (DC) power source. Inside the device is a framework 501 to which the mechanical parts of the device are attached. Attached to the framework 501 is a small DC motor 502 with a motor shaft 503, which drives the stimulation mechanism. A screw shaft 504 is affixed directly to the motor shaft 503 of the DC motor 502, such that the screw shaft 504 rotates as the motor shaft 503 of the DC motor 502 rotates. The polarity of voltage to the DC motor 502 may be reversed so that the motor shaft 503 of the DC motor 502 rotates both clockwise and counter-clockwise. In this embodiment, the flex coupling 105 has been eliminated, allowing the device to be constructed in a more compact form, approximately 2 cm shorter in overall length. A nut 505 is placed around the screw shaft 504 and attached to a bracket 506, which is held in a particular orientation by guide rods 507, such that the nut 505 and bracket 506 travel in a linear motion as the screw shaft 504 is turned. Affixed to the bracket 506 is a gripper 508, which travels in a linear motion along with the bracket 506. A hole 509 in the framework 501, allows for the insertion of a flexible sleeve 201 as previously shown in FIG. 2. Magnetic sensors 511 may be used to set limits of operation of the nut 506, or to ensure that the nut 506 is at one end of its range of motion before starting operation of the device. An integrated circuit (not visible in drawing) 512 may be used to control the operation of the device.

Figure 6:
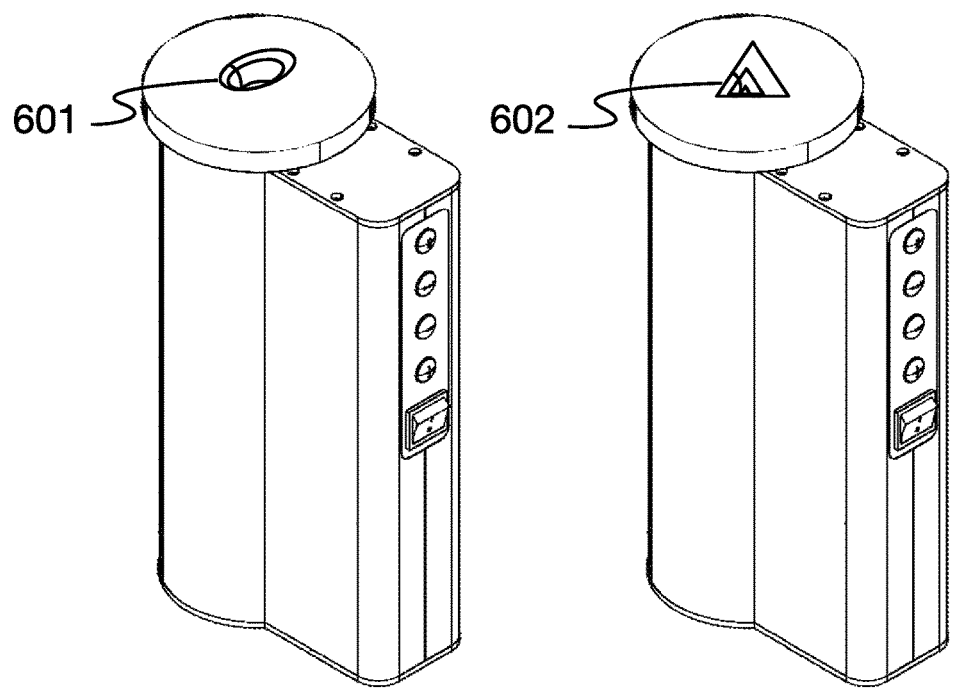
FIG. 6 shows additional exemplary variations of the sleeve aspect of an exemplary male sexual stimulation device as set forth in another preferred embodiment.

FIG. 6 shows additional exemplary variations 600 of the sleeve aspect of an exemplary male sexual stimulation device as set forth in another preferred embodiment. In this embodiment, the opening in the sleeve may be other than circular. For example, the opening may be elliptical in shape 601 or triangular in shape 602.

Figure 7:
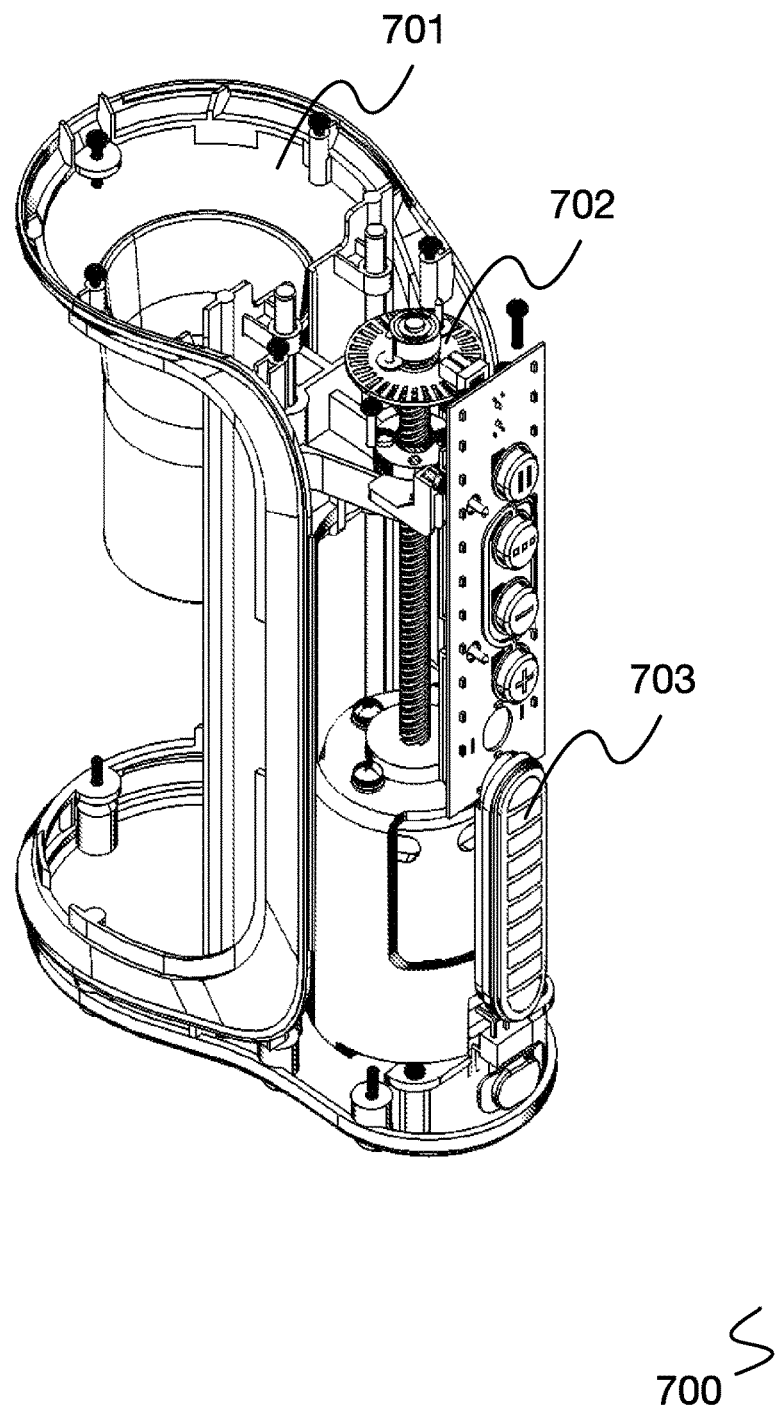
FIG. 7 shows additional features of an exemplary male sexual stimulation device according to another preferred embodiment.

FIG. 7 shows additional features of an exemplary male sexual stimulation device according to another preferred embodiment 700. In this embodiment, the framework 701 is made from a molded plastic structure. An optical rotary encoder 702 is used to determine the rotational speed and number of rotations of the screw shaft to control patterns of stimulation. A series of light emitting diodes (LEDs) 703 are used to indicate the mode of operation of the device.

Optionally, the device may include a number of other functions to enhance the user experience. For example, a grippable surface may be molded to the outside of the housing to provide better grip in the hand. The device may contain the ability to warm the sheath to an optimal temperature prior to and during use. The device may also contain additional methods of stimulation in addition to the primary linear motion, such as suction, vibration, or direct electrical stimulation. The device may be made more portable by designing it to operate from batteries contained within the device housing. It will be apparent to one skilled in the art, that the linear motion could be generated by some other means than a rotary electric motor.

One or more different aspects may be described in the present application. Further, for one or more of the aspects described herein, numerous alternative arrangements may be described; it should be appreciated that these are presented for illustrative purposes only and are not limiting of the aspects contained herein or the claims presented herein in any way. One or more of the arrangements may be widely applicable to numerous aspects, as may be readily apparent from the disclosure. In general, arrangements are described in sufficient detail to enable those skilled in the art to practice one or more of the aspects, and it should be appreciated that other arrangements may be utilized and that structural, logical, software, electrical and other changes may be made without departing from the scope of the particular aspects. Particular features of one or more of the aspects described herein may be described with reference to one or more particular aspects or figures that form a part of the present disclosure, and in which are shown, by way of illustration, specific arrangements of one or more of the aspects. It should be appreciated, however, that such features are not limited to usage in the one or more particular aspects or figures with reference to which they are described. The present disclosure is neither a literal description of all arrangements of one or more of the aspects nor a listing of features of one or more of the aspects that must be present in all arrangements.

Headings of sections provided in this patent application and the title of this patent application are for convenience only, and are not to be taken as limiting the disclosure in any way.

Devices that are in communication with each other need not be in continuous communication with each other, unless expressly specified otherwise. In addition, devices that are in communication with each other may communicate directly or indirectly through one or more communication means or intermediaries, logical or physical.

A description of an aspect with several components in communication with each other does not imply that all such components are required. To the contrary, a variety of optional components may be described to illustrate a wide variety of possible aspects and in order to more fully illustrate one or more aspects. Similarly, although process steps, method steps, algorithms or the like may be described in a sequential order, such processes, methods and algorithms may generally be configured to work in alternate orders, unless specifically stated to the contrary. In other words, any sequence or order of steps that may be described in this patent application does not, in and of itself, indicate a requirement that the steps be performed in that order. The steps of described processes may be performed in any order practical. Further, some steps may be performed simultaneously despite being described or implied as occurring non-simultaneously (e.g., because one step is described after the other step). Moreover, the illustration of a process by its depiction in a drawing does not imply that the illustrated process is exclusive of other variations and modifications thereto, does not imply that the illustrated process or any of its steps are necessary to one or more of the aspects, and does not imply that the illustrated process is preferred. Also, steps are generally described once per aspect, but this does not mean they must occur once, or that they may only occur once each time a process, method, or algorithm is carried out or executed. Some steps may be omitted in some aspects or some occurrences, or some steps may be executed more than once in a given aspect or occurrence.

When a single device or article is described herein, it will be readily apparent that more than one device or article may be used in place of a single device or article. Similarly, where more than one device or article is described herein, it will be readily apparent that a single device or article may be used in place of the more than one device or article.

The functionality or the features of a device may be alternatively embodied by one or more other devices that are not explicitly described as having such functionality or features. Thus, other aspects need not include the device itself.

Techniques and mechanisms described or referenced herein will sometimes be described in singular form for clarity. However, it should be appreciated that particular aspects may include multiple iterations of a technique or multiple instantiations of a mechanism unless noted otherwise. Process descriptions or blocks in figures should be understood as representing modules, segments, or portions of code which include one or more executable instructions for implementing specific logical functions or steps in the process. Alternate implementations are included within the scope of various aspects in which, for example, functions may be executed out of order from that shown or discussed, including substantially concurrently or in reverse order, depending on the functionality involved, as would be understood by those having ordinary skill in the art.

What is claimed is:

1. A male sexual stimulation device comprising:
   a framework made of a rigid material or rigid materials;
   a reversible electric motor with a rotating shaft affixed to the framework;
   a threaded screw shaft mechanically connected to the shaft of the electric motor;
   a threaded nut screwed onto the threaded screw shaft;
   a tubular or annular gripper affixed to the threaded nut; and a removable, flexible sleeve, tubular in shape and open on one end, configured to be inserted into the tubular or annular gripper, with flanges on the outer surface of the sleeve configured to mechanically affix a portion of the removable, flexible sleeve to the tubular or annular gripper during use; and wherein, when the device is activated, the electric motor turns the threaded screw shaft clockwise and counter-clockwise, causing the nut and the affixed tubular or annular gripper to move in an axial linear motion, causing a portion of the removable, flexible sleeve to move in an axial linear motion along a penis which has been inserted into the removable, flexible sleeve.

2. The device of claim 1, wherein the device further comprises a heating apparatus that warms the flexible sleeve to an optimal temperature.

3. The device of claim 1, wherein the device further comprises a suction mechanism that provides stimulation in addition to the linear motion stimulation.

4. The device of claim 1, wherein the device further comprises a vibration mechanism that provides stimulation in addition to the linear motion stimulation.

5. The device of claim 1, wherein the device further comprises a direct electrical stimulation mechanism that provides stimulation in addition to the linear motion stimulation.

* * * * *